(12) United States Patent
Biscardi

(10) Patent No.: US 7,244,024 B2
(45) Date of Patent: Jul. 17, 2007

(54) EYE TARGET APPARATUS

(76) Inventor: Henry M. Biscardi, 4461 Tule Lake Dr., Littleton, CO (US) 80123

( * ) Notice: Subject to any disclaimer, the term of this patent is extended or adjusted under 35 U.S.C. 154(b) by 677 days.

(21) Appl. No.: 10/708,237

(22) Filed: Feb. 18, 2004

(65) Prior Publication Data

US 2005/0179866 A1 Aug. 18, 2005

(51) Int. Cl.
*A61B 3/10* (2006.01)
*A61B 3/02* (2006.01)
*A61B 3/14* (2006.01)
*A61B 17/00* (2006.01)

(52) U.S. Cl. ............ 351/211; 351/205; 351/208; 351/212; 351/222; 351/242; 606/1; 606/5

(58) Field of Classification Search ............ 351/205, 351/206, 208, 210–214, 218, 221–224, 237, 351/242, 243, 246; 606/1, 2, 5; 128/858; 600/248
See application file for complete search history.

(56) References Cited

U.S. PATENT DOCUMENTS

| | | | | |
|---|---|---|---|---|
| 1,889,456 A * | 11/1932 | Tillyer | ................. | 351/205 |
| 4,776,045 A | 10/1988 | Mysliwiec et al. | ........... | 2/426 |
| 4,856,513 A * | 8/1989 | Muller | ................. | 606/5 |
| 4,862,902 A | 9/1989 | Goffman | ............... | 128/858 |
| 5,092,863 A * | 3/1992 | Schanzlin | ............ | 606/5 |
| 5,264,877 A | 11/1993 | Hussey | .................. | 351/45 |
| 5,402,188 A | 3/1995 | Wayne | ................... | 351/43 |
| 5,461,436 A | 10/1995 | Campbell | ............. | 351/242 |
| 5,714,751 A | 2/1998 | Chen | ................. | 250/203.4 |
| 5,769,806 A | 6/1998 | Radow | .................. | 602/41 |
| 5,805,270 A | 9/1998 | Marshall | ............. | 351/222 |
| 6,401,050 B1 | 6/2002 | Cooke et al. | .......... | 702/127 |
| 6,869,427 B1 * | 3/2005 | Shokoohi | ............. | 606/1 |
| 6,945,650 B2 * | 9/2005 | Beverly | ............... | 351/208 |
| 2002/0198577 A1 | 12/2002 | Jaillet | .................. | 607/88 |
| 2003/0056281 A1 | 3/2003 | Hasegawa | ............ | 2/428 |

* cited by examiner

*Primary Examiner*—Loha Ben
(74) *Attorney, Agent, or Firm*—Roger A. Jackson

(57) ABSTRACT

An eye target apparatus and method helping to control an operative eye focus line of sight position during medical procedures on the operative eye of a cooperative awake patient. The apparatus includes a housing for occluding substantially all visual perception from an exterior environment for a non operative eye, the housing including a cover, with an internal surface that forms a plane approximately perpendicular to the non operative eye line of sight axis. Also included is a visually perceptible element adjacent to the internal surface being in visual communication with the non operative eye and structure for moving the visually perceptible element within the plane to any selected position, the apparatus is operational to help the non operative eye focus on a selected line of sight position upon the visually perceptible element with the result in assisting in the operative eye achieving a stable selected line of sight position.

28 Claims, 11 Drawing Sheets

EYE TARGET APPARATUS

TECHNICAL FIELD

The present invention relates generally to apparatus that occludes an eye for the purpose of helping to control the positioning of a non occluded eye during medical procedures being performed upon the non occluded eye. More particularly, the present invention relates specifically to an eye target apparatus that helps control a selected focus line of sight axis position and line of sight axis position stability of the occluded eye thereby helping to control the non occluded eye or operative eye that has medical procedures performed upon it, wherein the selected focus line of sight axis position and line of sight position stability of the operative eye acts in conjunction with the occluded or non operative eye by both of the patient's eyes generally acting in coordination.

BACKGROUND OF INVENTION

There are a number of medical procedures that are performed on a patient's eye (termed operative eye) such as cataract removal, lens implants, vision corrective surgery, injury repair, and the like, wherein the aforementioned medical procedures typically require bright high-intensity operative lighting that is focused upon the operative eye for the eye surgeon and others to perform their task. Also, it can be important that the operative eye assume a selected particular focus line of sight axis position and be stable in that particular focus line of sight axis position, in addition, during the medical procedure the eye surgeon and others may require that the operative eye be moved to a second selected particular focus line of sight axis position, and so on. The patient may be under local anesthesia during the medical procedure on their operative eye. Depending upon the medical procedure performed on the operative eye and the level of anesthesia, the bright high-intensity operative lighting that is focused upon the operative eye, that typically has diminished visual acuity from the medical procedure, can be disorientating and uncomfortable for the awake patient in addition to possibly causing the operative eye to change its focus line of sight position unexpectedly and/or cause the operative eye to move uncontrollably, making the eye surgery more difficult and lengthy potentially causing additional medical complications.

Although, the aforementioned problem is recognized, the prior art has not directly addressed this issue, however, there are some prior art devices that occlude an eye or impart various visual images to the eye for the purpose of field of vision testing, eye therapy, brain activity testing, sports timing or pacing, and the like. Principally, the prior art most focuses upon field of vision testing, an example would be in U.S. Pat. No. 5,805,270 to Marshall that discloses a device and method for field of vision testing that includes a patch and an opaque eye cover housing with an array of fixed position LED's with selected and sequential illumination. Marshall observes the non occluded eye movement in responding to the occluded eye reacting to various illumination points. Another example is in a more conventional field of vision testing device in U.S. Pat. No. 5,461,436 to Campbell that discloses an open chamber that both of the patient's eyes see and thus both of the patient's eyes see the same background color allowing color field of vision testing thus minimizing retinal rivalry interference, which is where the eye that is not the subject of the field of vision testing interferes with the vision of the eye being tested, such as when the eye not being tested is completely occluded and interferes with the vision of the eye being tested, being particularly troublesome when the patient has a dominant eye. Additionally, in Campbell if the non tested eye was exposed to a white light background, which was found to be too bright for some patient's, was also found to affect field of vision test results. Campbell attempts to overcome these problems by providing a non white background light for the non tested eye, which is claimed to be more effective in detecting glaucoma with the preferred colors being a yellow background for both eyes and a blue spot fixation light for the tested eye that is movable for field of vision testing.

In the brain activity area, in U.S. patent application publication number U.S. 2002/0198577 A1 to jaillet disclosed is a monocular apparatus for selectively stimulating brain activity of a patient by the use of light and/or sound for diagnosis of the extent of brain injury, or other brain disorder. Jaillet in one embodiment is an eye glasses type of structure having a plurality of fixed position lights that in conjunction with or without sound or having sound alone, all or part of which are selectively activated to stimulate the brain in either one or both eyes with the light stimulation varying in color intensity and frequency. On the therapy side for defects in eye vision in U.S. Pat. No. 5,264,877 to Hussey, disclosed is a pair of eyeglasses that have a selectable opaque to transparent view and vice versa single lens that are adjacent to a thin film, being a liquid crystal type display sandwiched between two metalized mylar films that are electrically controlled that in effect align the liquid crystals changing the thin film from transparent to opaque and vice versa at a high frequency. Hussey is for the treatment of cross eye and lazy eye, wherein the objective of the treatment is to stimulate the subservient eye. Also, in the eye therapy area in U.S. patent application publication number U.S. 2003/0056281 A1 to Hasegawa, disclosed is an eye mask that has the capability of magnetic bodies, heating, cooling, vibrators, eyeball shapers, aromatics, sound, and elimination of sound for the treatment of eye fatigue, disease, pseudo myopia, moderate farsightedness, and moderate astigmatism. Hasegawa also controls the fixed position illumination bodies for frequency and intensity.

In the sports timing or pacing area in U.S. Pat. No. 5,402,188 to Wayne disclosed is an athletic pacing goggle that has a selectable periodic fixed position visual signal to a swimmer for the purpose of allowing the swimmer to pace their strokes. Wayne includes a fixed position LED in the swimming goggles that is in a corner of one eye, being in the peripheral field vision of that eye, the LED flashes at a selectable frequency for the swimmer to pace their strokes wherein the goggles of necessity remain transparent for both eyes. A similar prior art example is in U.S. Pat. No. 4,776,045 to Mysliwiec et al. that discloses an athletic pacing goggle that is similar to Wayne except that in addition to a periodic fixed position visual signal, a timing device is also in the swimmers peripheral field of vision, utilizing a special lens to better make the timing device readable, which is again for use in pacing swimming strokes and for measuring elapsed time for swimming laps.

The aforementioned prior art does not disclose a device that directly addresses the identified problems of the operative eye assuming a selected particular focus line of sight axis position and be stable in that particular focus line of sight axis position, or having a device to move the operative eye to a second selected focus line of sight axis position or positions and also helping to maintain the selected focus line of sight axis position in a stable manner for the purpose of more effective and efficient eye surgery for the patient.

SUMMARY OF INVENTION

Broadly, the present invention is an eye target apparatus for use in helping to control an operative eye focus line of sight axis position during medical procedures on the operative eye. The eye target apparatus includes a housing for occluding substantially all visual perception from an exterior environment for a non operative eye. The housing also includes a cover, the cover also having an internal surface that forms a plane positioned approximately perpendicular to the non operative eye focus line of sight axis. Also included is a visually perceptible element that is adjacent to the cover internal surface being in visual communication with the non operative eye. In addition, included is a means for moving the visually perceptible element within the plane to any selected position. The eye target apparatus is operational to help the non operative eye focus on a selected line of sight focus axis position upon the visually perceptible element with the result in assisting in the operative eye achieving a stable selected line of sight focus axis position with minimal operative eye movement from the selected line of sight focus axis position.

These and other objects of the present invention will become more readily appreciated and understood from a consideration of the following detailed description of the exemplary embodiment(s) of the present invention when taken together with the accompanying drawings, in which;

REFERENCE NUMBER IN DRAWINGS

Figure 1:
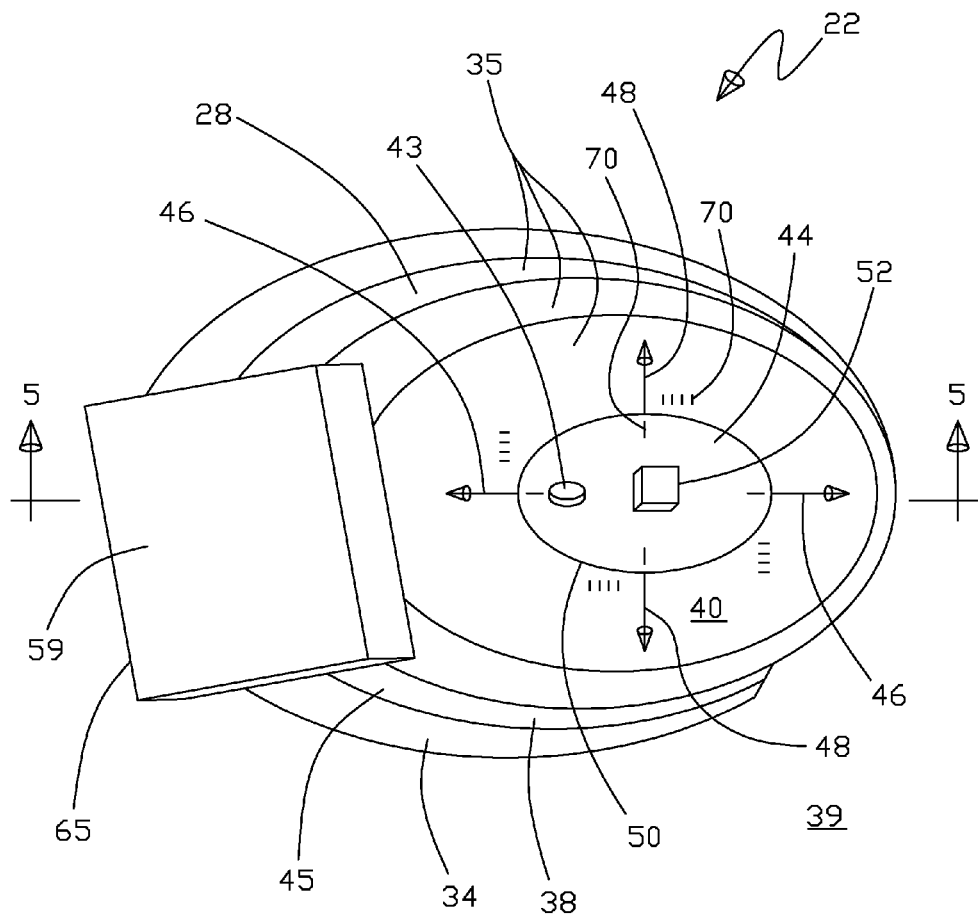
FIG. 1 shows a perspective view of the eye target apparatus as viewed from the side opposite of the non operative eye side.

22 Eye Target Apparatus assembly
23 Eye Target Apparatus assembly alternative embodiment
24 Eye non operative
25 Eye lens non operative
26 Selected non operative eye line of sight focus axis position
27 Patient facial contours adjacent to the patient's non operative eye
28 Housing assembly
30 Housing cover internal surface
32 Housing plane
33 Housing opening
34 Housing flange portion
35 Housing exterior
36 Resilient housing mounting pad
37 Housing interior
38 Housing surrounding sidewall
39 Exterior environment
40 Housing cover
41 Housing cover aperture
42 Visually perceptible element
43 Lockable element
44 Means for moving the visually perceptible element within the plane
45 Housing surrounding sidewall end portion
46 Visually perceptible element X axis movement
47 Cap and cover slidable engagement
48 Visually perceptible element Y axis movement
49 Resilient housing mounting pad adhesive
50 Slidable cap
51 Slidable engagement between the housing cover and the slidable cap retainer element
52 Slidable cap finger grip
53 Slidable engagement between the cover retainer element and the slidable cap
54 Slidable cap retainer element facing the non operative eye
56 Slidable cap retainer element aperture for the visually perceptible element
57 Outer peripheral cover retainer element extension
58 Slidable cap retainer element extension
59 Circuitry
60 Electrical switch SW1
61 Resistor
62 Electrical power supply
63 Electrical communication between the circuitry 59 and the visually perceptible element 42
64 Cover retainer element
65 Circuitry housing
66 Cover retainer element aperture
68 Sterile package
70 Indicia
72 Operative eye
74 Operative eye line of sight focus axis position
76 Operating light, medical equipment, or device, sometimes termed microscope
77 Bright white light
78 Patient
80 Operating table
82 Sterile drape
100 Step of positioning patient
102 Step of locating medical device with a light source over the operative eye
104 Step of providing and placing eye target apparatus over the non operative eye 106 Step of patient opening both operative and non operative eyes for a selected period
108 Step of activating the eye target apparatus visually perceptible element
110 Step of confirming that patient observes the visually perceptible element in the central portion of the light source
112 Step of moving selectively the visually perceptible element to a desired point helping result in a selected operative eye focus line of sight axis as a reference
113 Step of performing the medical procedure on the operative eye
114 Step of instructing patient to move the operative eye focus line of sight axis relative to the visually perceptible element
116 Step of instructing patient to keep their operative and non operative eyes focused on the visually perceptible element during movement of the light source
150 Continuation of optional step 114 from step 113
152 Continuation of optional step 116 from step 113
154 Continuation of optional steps 114 and/or 116 returning to step 112

DETAILED DESCRIPTION

Figure 2:
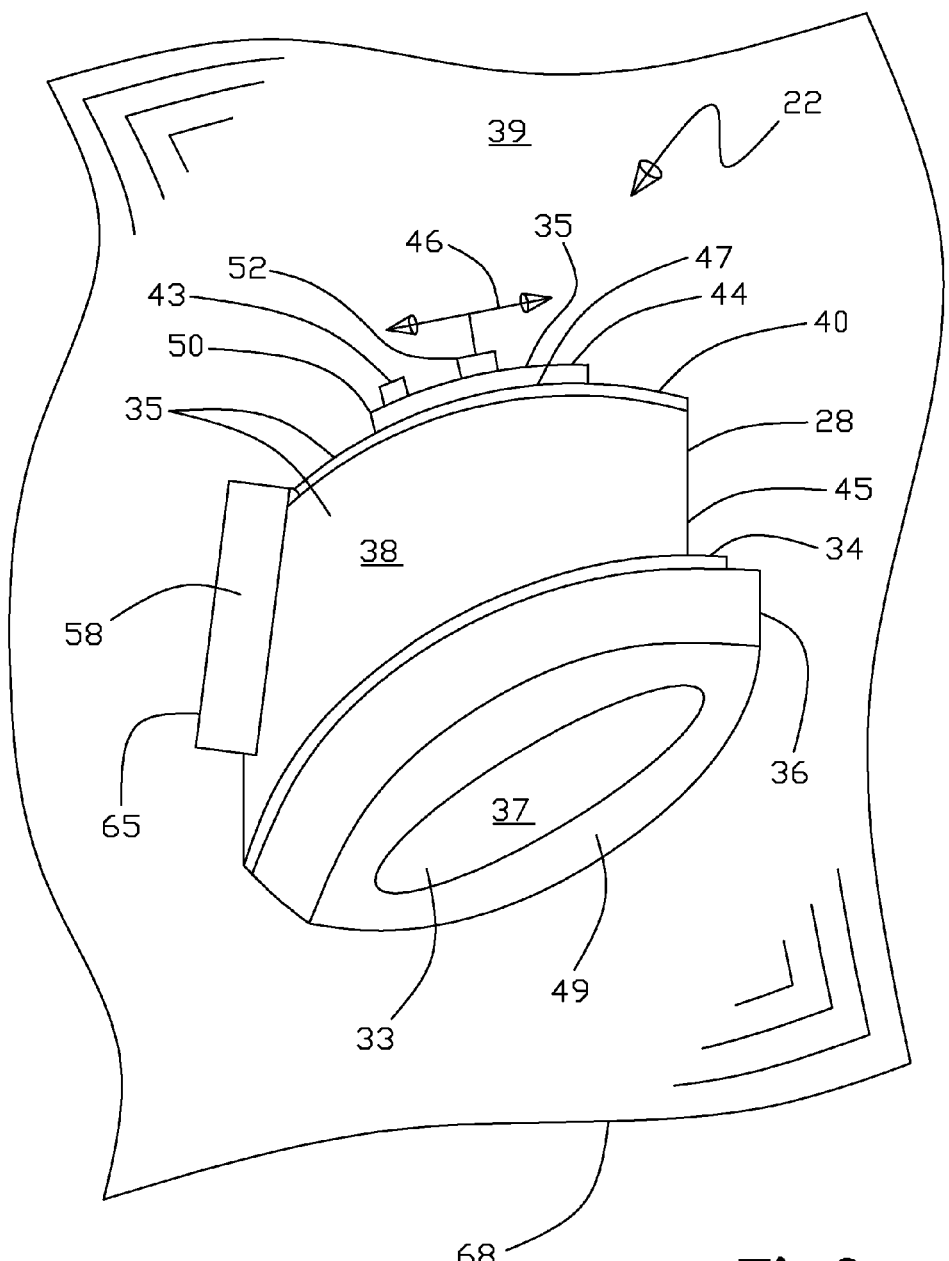
FIG. 2 shows a perspective view of the eye target apparatus as viewed from a side elevation.
Figure 3:
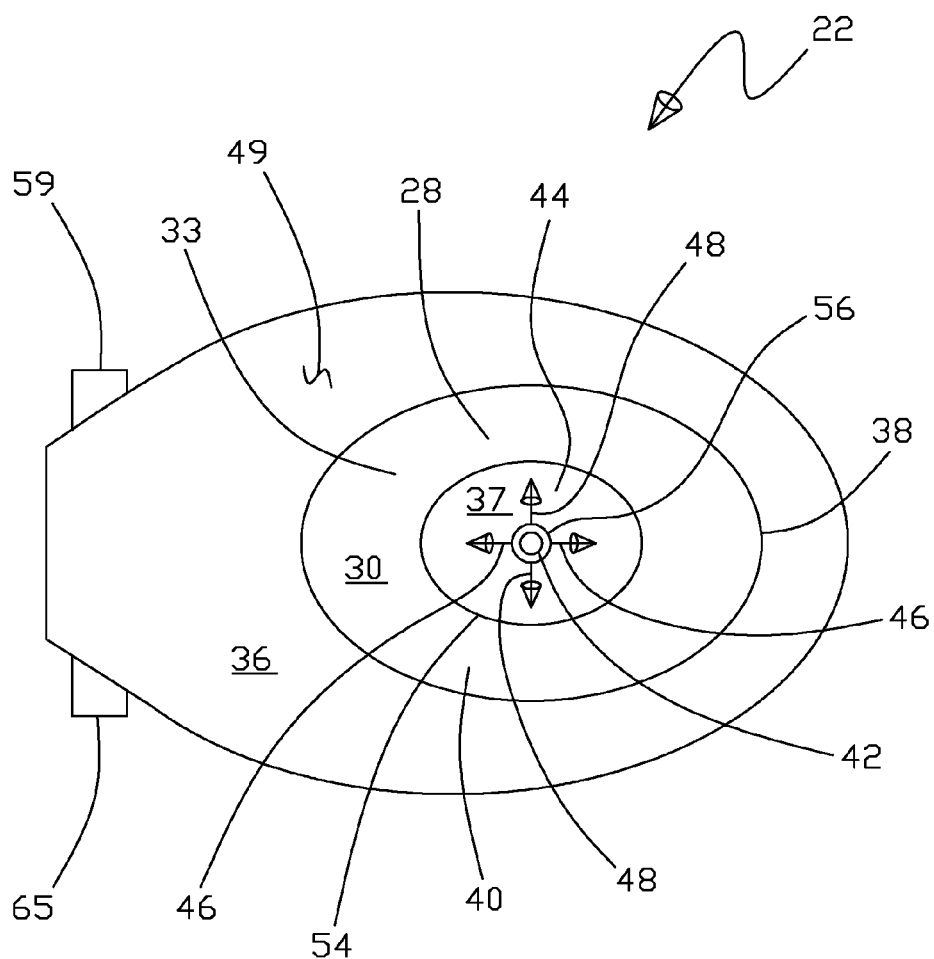
FIG. 3 shows a view of the eye target apparatus or the alternative embodiment of the eye target apparatus as viewed from the non operative eye side.
Figure 4:
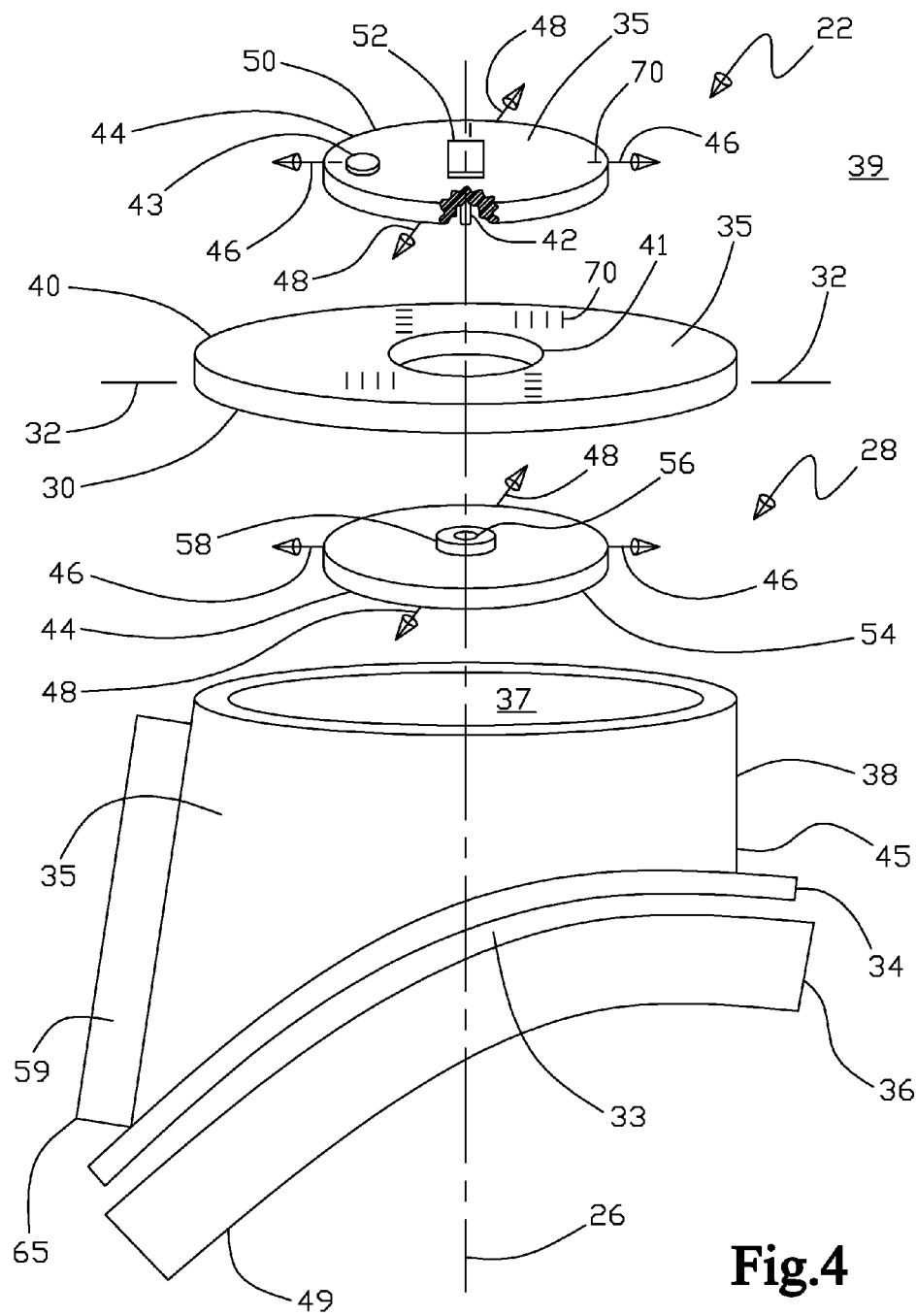
FIG. 4 shows an exploded perspective view of the eye target apparatus as viewed from a side elevation.
Figure 5:
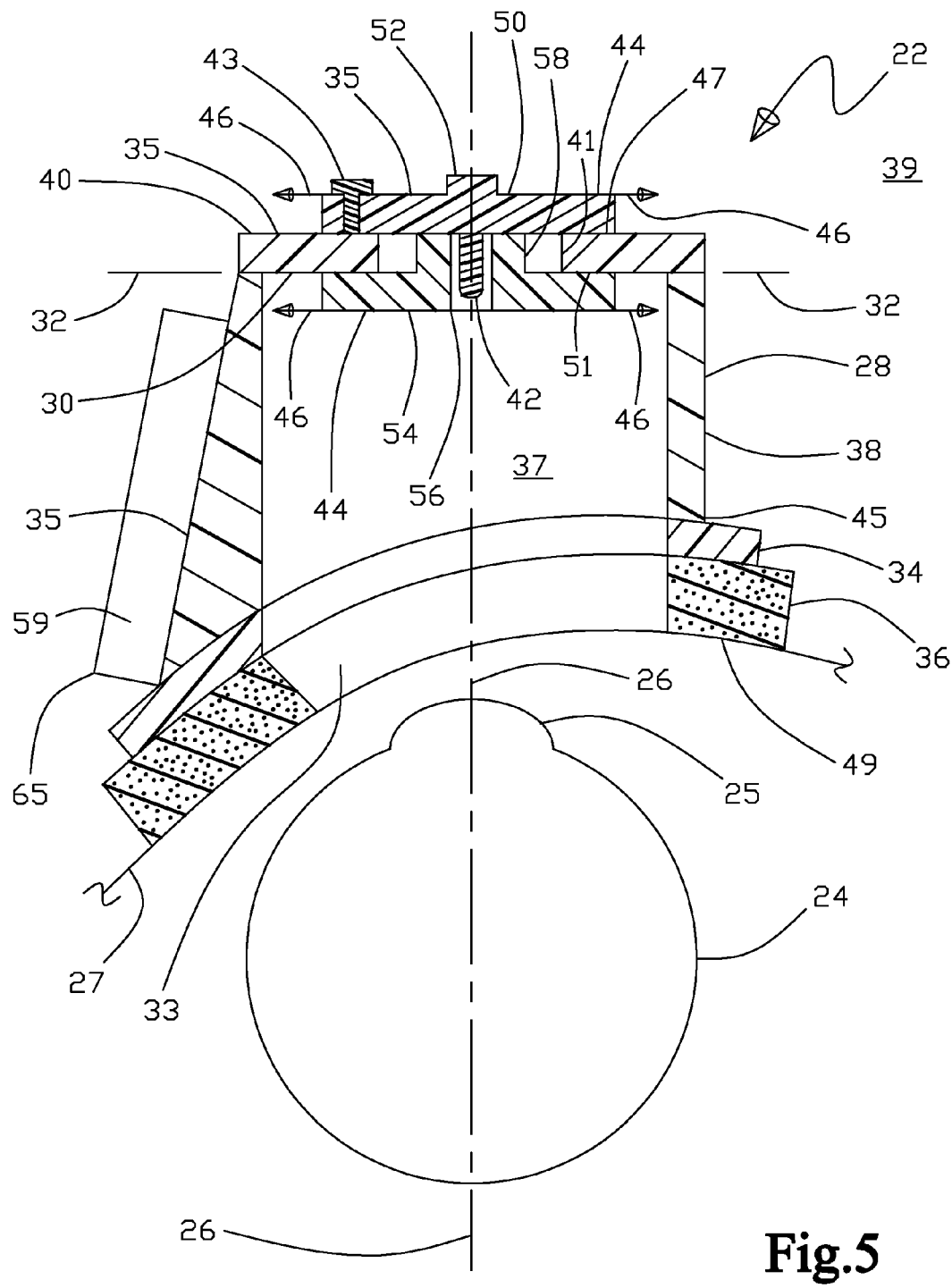
FIG. 5 shows cross-sectional view 5-5 from FIG. 1 of the eye target apparatus in use placed upon a patient's face over the non operative eye.
Figure 6:
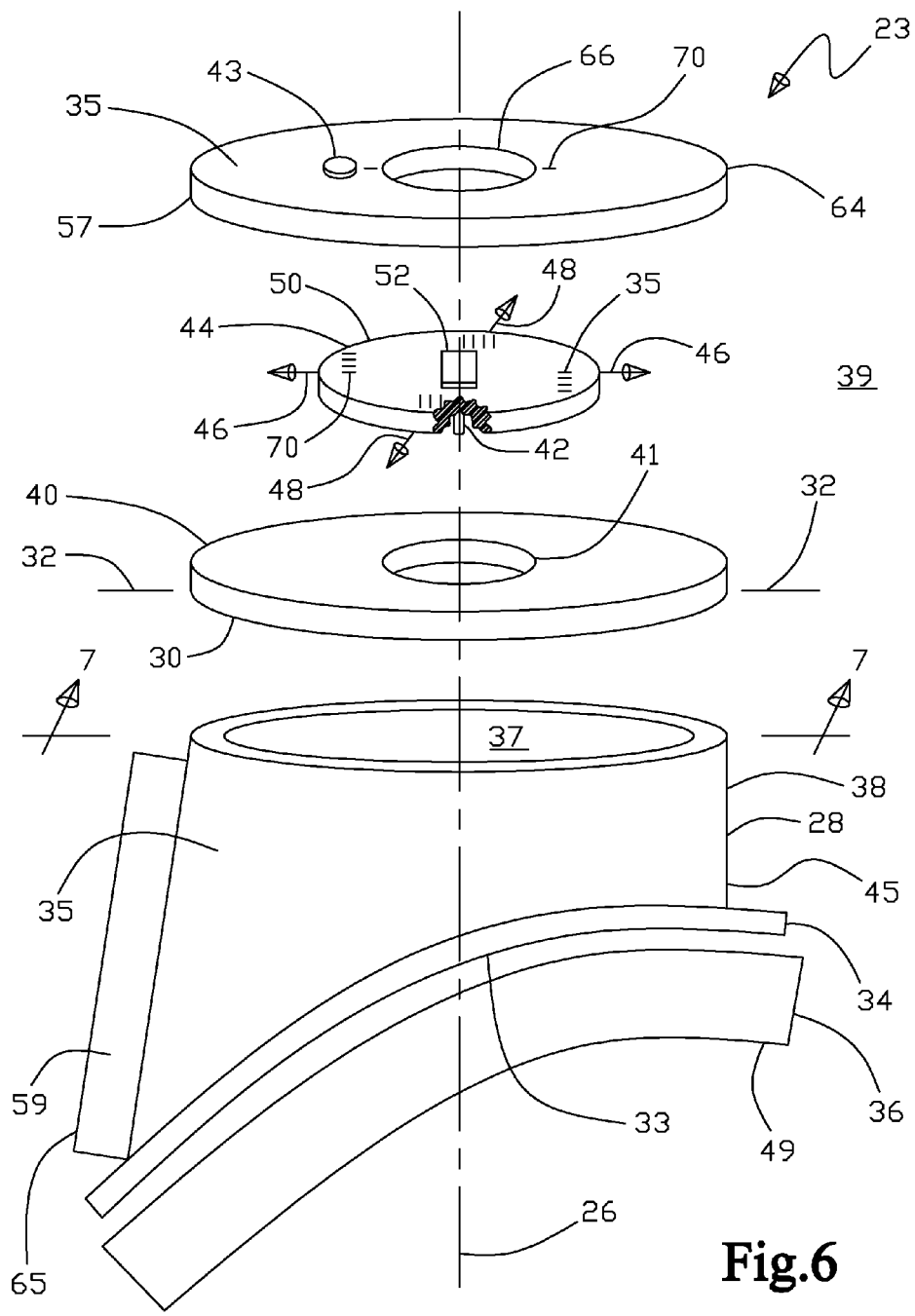
FIG. 6 shows an exploded perspective view of an alternative embodiment of the eye target apparatus as viewed from a side elevation.
Figure 7:
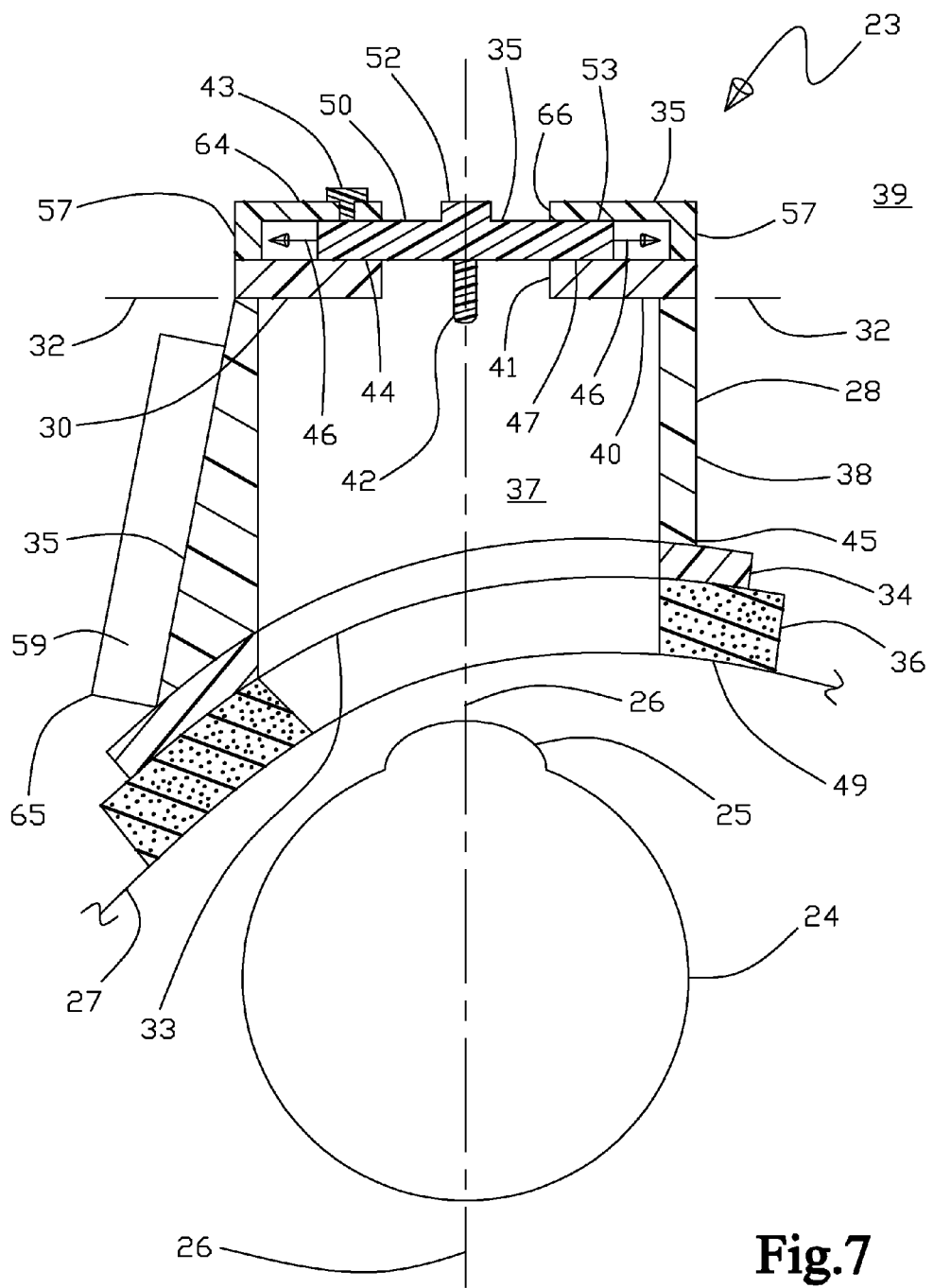
FIG. 7 shows cross-sectional view 7-7 from FIG. 6 of an alternative embodiment of the eye target apparatus in use placed upon a patient's face over the non operative eye.
Figure 8:
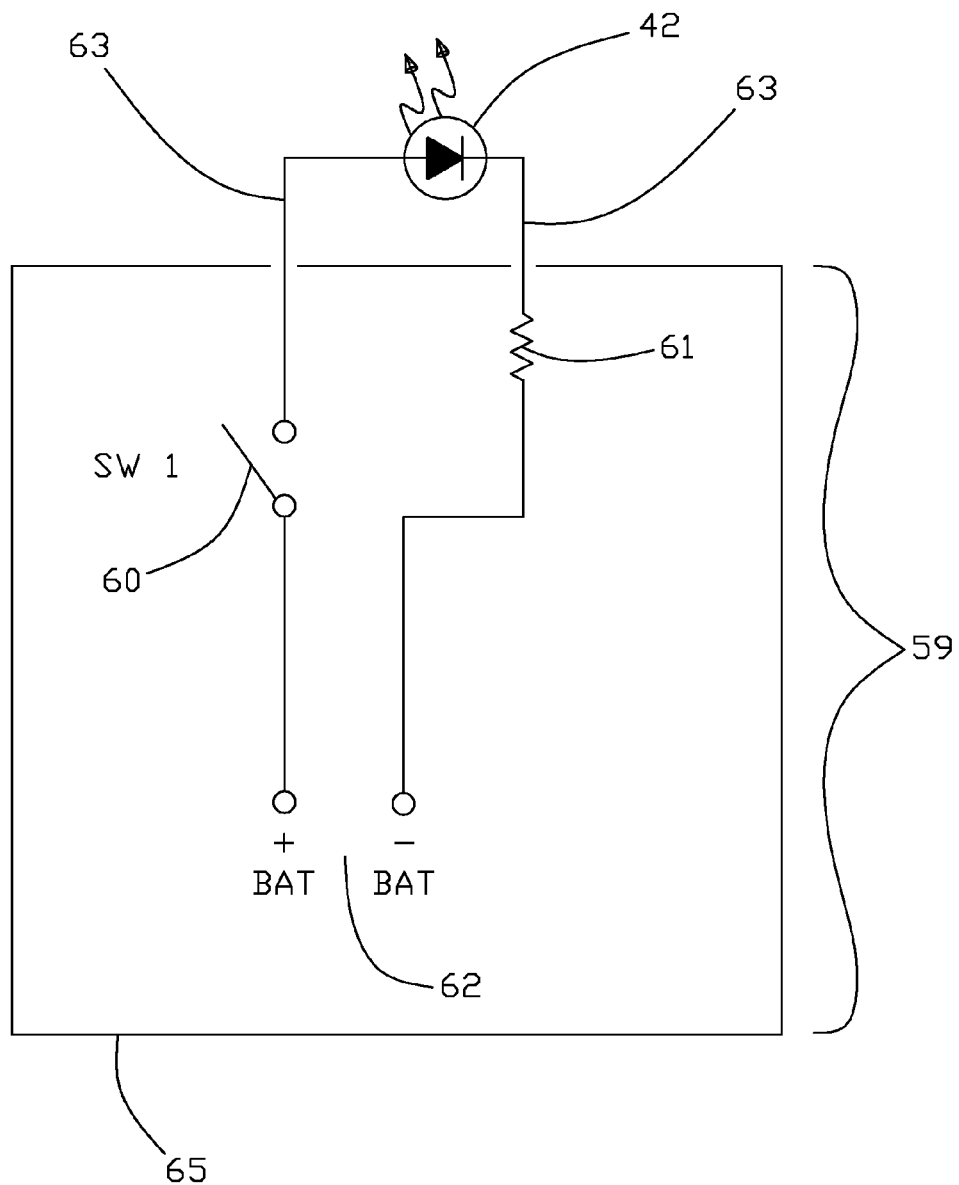
FIG. 8 shows an electrical schematic for the eye target apparatus.
Figure 9:
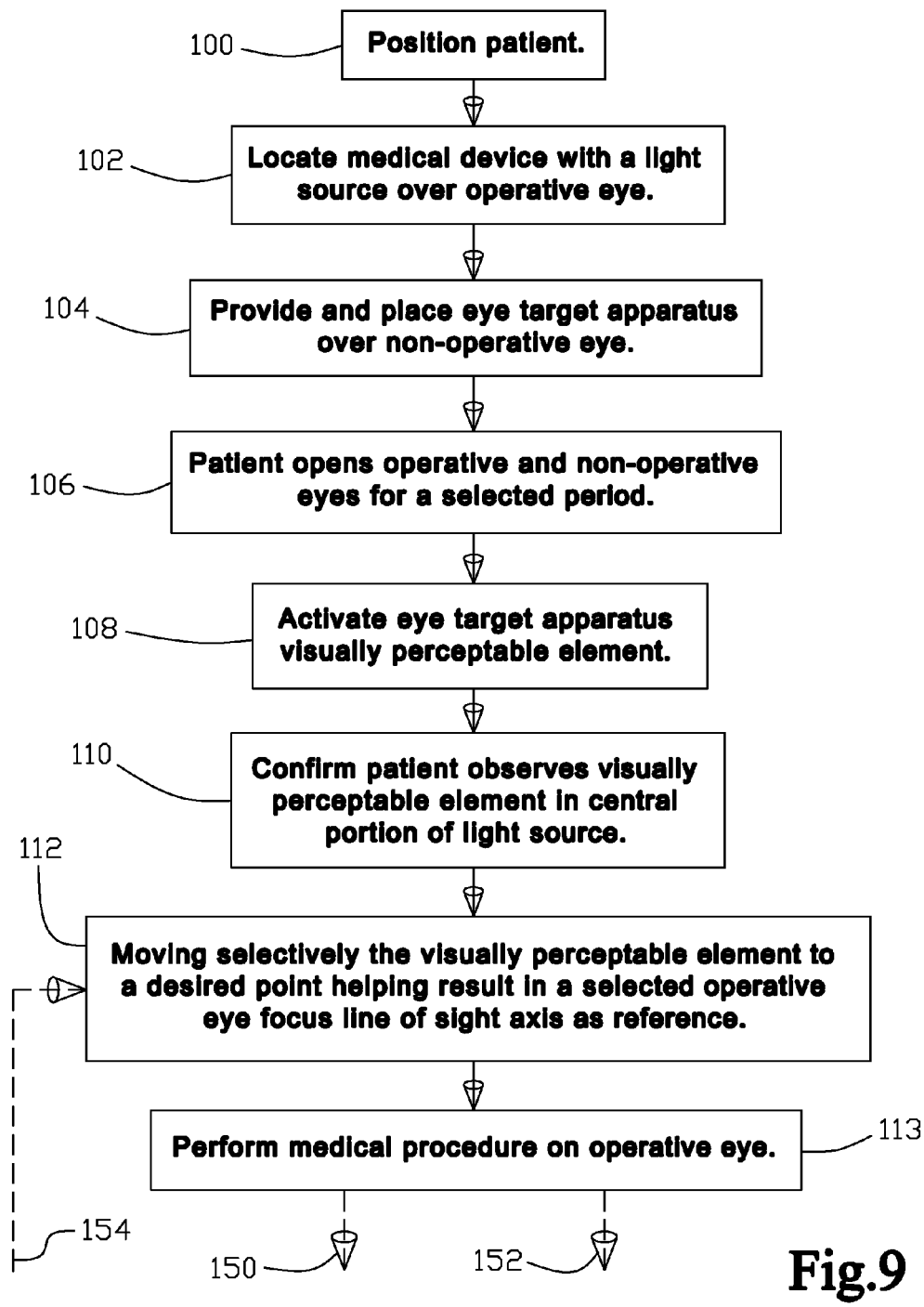
FIG. 9 is a flow chart illustrating diagrammatically the broad concepts according to the methodology of using the eye target apparatus.
Figure 10:
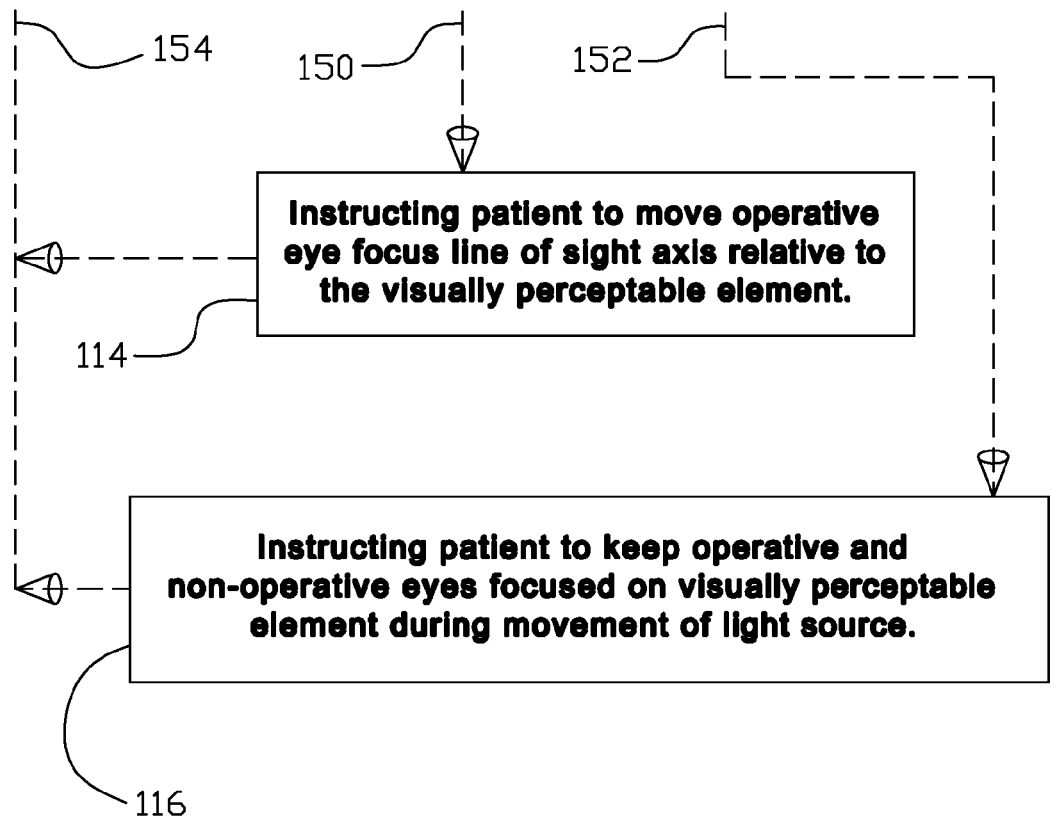
FIG. 10 is a continuation of FIG. 9 showing the flow chart illustrating diagrammatically the broad concepts according to the methodology of using the eye target apparatus.
Figure 11:
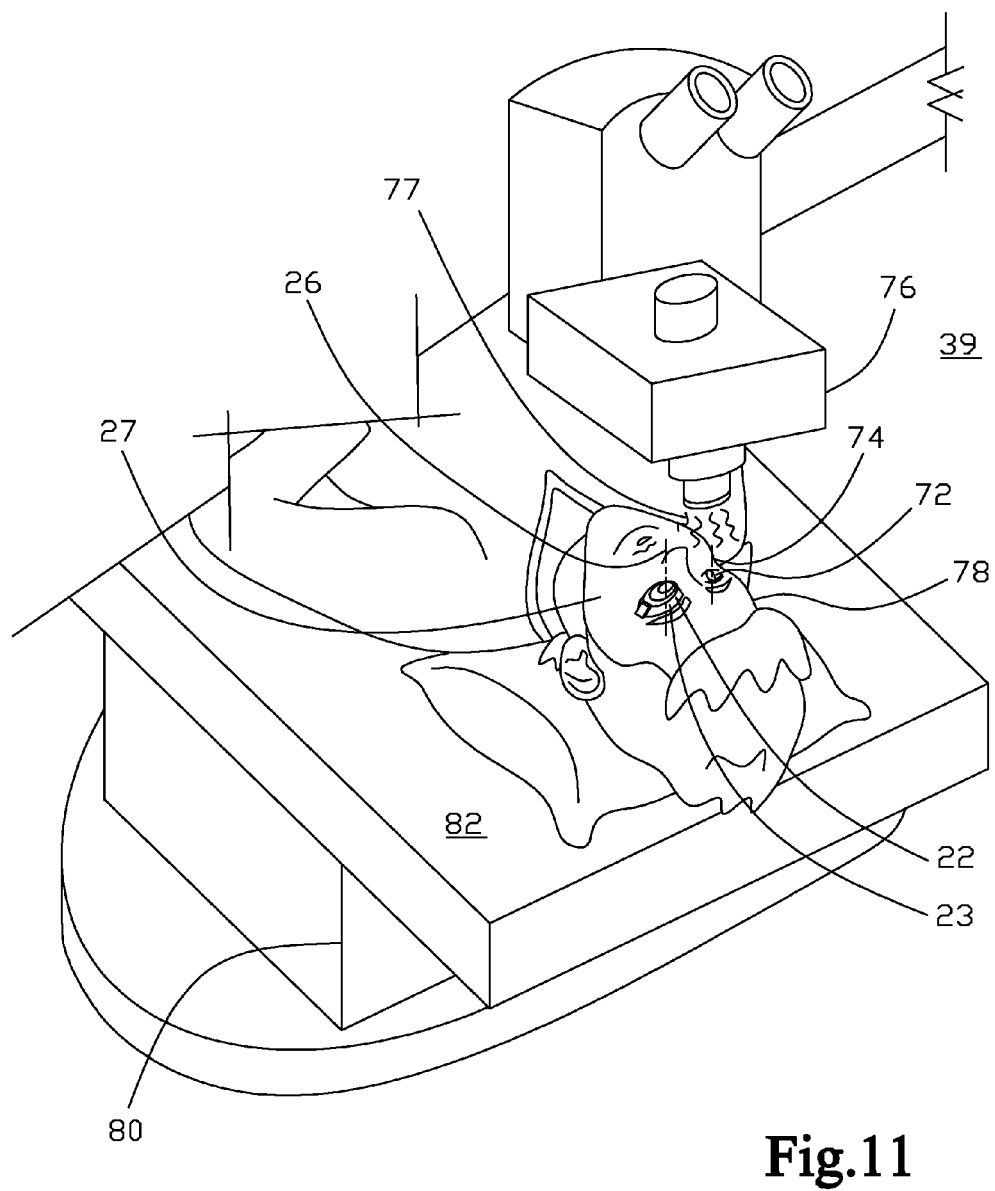
FIG. 11 is a use view showing either the eye target apparatus or the alternative embodiment of the eye target apparatus positioned on the patient's facial contour over the non operative eye with the patient's operative eye exposed to the white light source with the patient on the operating table.

With initial reference to FIGS. 1-11, the eye target apparatus 22 and the alternative embodiment of the eye target apparatus 23 are generally described, as an eye target apparatus 22 and the alternative embodiment of the eye target apparatus 23 being for use in helping to control an operative eye 72 focus line of sight axis 74 position during medical procedures on the operative eye 72. With FIG. 1 showing a perspective view of the eye target apparatus 22 as viewed from the side opposite of the non operative eye 24 side. FIG. 2 shows a perspective view of the eye target apparatus 22 as viewed from a side elevation and FIG. 3 shows a view of the eye target apparatus 22 as viewed from the non operative eye 24 side. Further, FIG. 4 shows an exploded perspective view of the eye target apparatus 22 as viewed from a side elevation and FIG. 5 shows cross-sectional view 5-5 from FIG. 1 of the eye target apparatus 22 in use placed upon a patient's 78 facial contour 27 over the non operative eye 24. Yet further, FIG. 6 shows an exploded perspective view of an alternative embodiment of the eye target apparatus 23 as viewed from a side elevation and FIG. 7 shows cross-sectional view 7-7 from FIG. 6 of the alternative embodiment of the eye target apparatus 23 in use placed upon a patient's 78 facial contour 27 over the non operative eye 24. FIG. 8 shows an electrical schematic for the eye target apparatus 22 and the alternative embodiment of the eye target apparatus 23 including circuitry 59 and a visually perceptible element 42. With FIG. 9 being a flow chart illustrating diagrammatically the broad concepts according to the methodology of using both the eye target apparatus 22 and the alternative embodiment of the eye target apparatus 23 and FIG. 10 being a continuation of FIG. 9 showing the flow chart illustrating diagrammatically the broad concepts according to the methodology of using both the eye target apparatus 22 and the alternative embodiment of the eye target apparatus 23. Further, FIG. 11 shows a use view showing either the eye target apparatus 22 or the alternative embodiment of the eye target apparatus 23 positioned on the patient's 78 facial contour 27 over the non operative eye 24 (hidden in FIG. 11 by the eye target apparatus 22 or 23) with the patient's 78 operative eye 72 exposed to the bright white light 77 of the operating light, medical equipment, or device 76 with the patient 78 in a supine position on the operating table 80 with a sterile drape 82 placed over the patient 78 with only the patient's 78 operative eye 72 and non operative eye 24 exposed.

Broadly, the present invention of the eye target apparatus 22 and the alternative embodiment of the eye target apparatus 23 both comprise a housing 28 for occluding substantially all visual perception from an exterior environment 39 for the non operative eye 24. The housing 28 includes a cover 40, with the cover 40 also including an internal surface 30 that forms a plane 32 that is positioned approximately perpendicular to the non operative eye 24 focus line of sight axis 26. Also included, is a visually perceptible element 42 adjacent to the cover 40 internal surface 30 that is in visual communication with the non operative eye 24. Further included is a means 44 for moving the visually perceptible element 42 within the plane 32 to any selected position. Wherein the eye target apparatus 22 and the alternative embodiment of the eye target apparatus 23 are operational to help the non operative eye 24 focus on a selected line of sight focus axis 26 position upon the visually perceptible element 42 with the result in assisting in the operative eye 72 (as shown in FIG. 11) achieving a stable selected line of sight focus axis 74 (as shown in FIG. 11) position with minimal operative eye 72 movement from the selected line of sight focus axis 74 position. Wherein, the selected focus line of sight axis 74 position and line of sight focus axis 74 position stability of the operative eye 72 acts in conjunction with the occluded or non operative eye 24 line of sight focus axis 26 position by both of the patient's 78 eyes being the non operative eye 24 and the operative eye 72 generally acting in coordination.

More particularly, on the housing 28 for both the eye target apparatus 22 and the alternative embodiment of the eye target apparatus 23, the housing 28 is preferably constructed of a surrounding sidewall 38 extending from the cover 40 to define a housing interior 37 separated from the exterior environment 39. The surrounding sidewall 38 also includes an end portion 45 opposite of the cover 40 that creates an opening 33 that communicates between the housing interior 37 and the exterior environment 39. The materials of construction for the housing 28, including the surrounding sidewall 38 and cover 40 are preferably polyethylene, polypropylene, polyurethane, or other like plastic materials, that are typically injection molded, or other materials that are suitable for sterile medical use and have the ability to occlude substantially all transmission of light. Further, on the housing 28 for both the eye target apparatus 22 and the alternative embodiment of the eye target apparatus 23 the housing 28 also preferably includes a flange portion 34 adjacent to the surrounding sidewall 38 end portion 45. The flange portion 34 is operational to rest against a patient's 78 facial contour 27 adjacent to the non operative eye 24. The materials of construction for the flange portion 34 are preferably as described for the surrounding sidewall 38, with the flange portion 34 being either integral, affixed, or removably attachable from the surrounding sidewall 38 end portion 45. Additionally, on the housing 28 for both the eye target apparatus 22 and the alternative embodiment of the eye target apparatus 23 there is preferably included a resilient housing mounting pad 36 that is adjacent to the flange portion 34. The mounting pad 36 is operational to comfortably conform to a patient's 78 facial contour 27 adjacent to the non operative eye 24. The materials of construction for the mounting pad 36 are preferably a closed cell or open cell foam rubber that is suitable for sterile medical use that also occludes substantially all transmission of light. The mounting pad 36 can either be integral, affixed, or removably attachable to the flange portion 34. As a further preferred refinement on the housing 28 for both the eye target apparatus 22 and the alternative embodiment of the eye target apparatus 23 further included on the resilient housing mounting pad 36 on a side opposite of the flange portion 34 is an adhesive 49. The adhesive 49 is operational to removably attach the resilient housing mounting pad 36 to the patient's 78 facial contour 27 adjacent to the non operative eye 24. Again, the adhesive 49 is preferably suitable for sterile medical use that also occludes substantially all transmission of light. The adhesive 49 can either be integral, affixed, or removably attachable to the resilient housing mounting pad 36.

Further, more particularly on the visually perceptible element 42, as applied to both the eye target apparatus 22 and the alternative embodiment of the eye target apparatus 23 the visually perceptible element 42 is preferably a color that is visually perceptible or visually distinguishable as against a white background light 77 of the operating light, medical equipment, or device 76 to allow the non operative eye 24 to focus upon the visually perceptible element 42 thus establishing a selected non operative eye 24 line of sight focus axis 26 position generally resulting in a like operative eye 72 (as shown in FIG. 11) line of sight focus axis 74 (as shown in FIG. 11) position, as the patient's 78 eyes normally act in coordination for movement and stability in remaining in the selected line of sight focus axis position(s) or a further selected line of sight focus axis position(s) and with both the non operative eye 24 and the operative eye 72 remaining more stable at the selected line of sight focus axis position (s). Also, as applied to both the eye target apparatus 22 and the alternative embodiment of the eye target apparatus 23 the visually perceptible element 42 is preferably a light emitting diode (LED) including circuitry 59 being contained within a circuitry housing 65, that is in electrical communication with the visually perceptible element 42 light emitting diode (LED), with the circuitry 59 being disposed within the circuitry housing 65 on an exterior 35 of the housing 28. The visually perceptible element 42 could also be something other than a LED, as long as the functional requirements of preferably being visually distinguishable as against a white background light 77 of the operating light, medical equipment, or device 76 to allow the non operative eye 24 to focus upon the visually perceptible element 42 were meet. The visually perceptible element 42 could also be an aperture in place of the LED that allows ambient environmental 39 light or light from the bright white light 77. The circuitry housing 65 is preferably constructed of materials similar to the housing 28.

Although FIGS. 1 through 7 show the circuitry 59 and housing 65 positioned adjacent to the housing 28 surrounding sidewall 38, the circuitry 59 and housing 65 could be positioned anywhere upon the exterior 35 of the housing 28 including the housing 28 cover 40, or for the eye target apparatus 22 on a slidable cap 50, or for the alternative embodiment of the eye target apparatus 23 on the cover retainer element 64 or on the slidable cap 50. The circuitry 59 electrical schematic is shown in FIG. 8 as including an electrical power supply 62, an electrical switch 60, a resistor 61, and the visually perceptible element 42 being preferably a light emitting diode (LED). The visually perceptible element 42 is preferably external to the housing 65 to allow visual communication between the visually perceptible element 42 and the non operable eye 24. The electrical power supply 62 is preferably a battery, being a watch or calculator type such as an EVEREADY ENERGIZER model Number CR2032 with an output of three (3) volts Direct Current (DC) or a like equivalent. Additionally, the electrical power supply 62 could be external to the circuitry 59, such as a converter that can utilize standard household electrical power of one hundred ten (110) volt and/or two hundred twenty (220) volt alternating current (AC) power that is converted to about three (3) volts (DC) for the circuitry 59 requirements as is well known in the electrical arts. The electrical switch 60 can be any control that is operative to activate the visually perceptible element 42 or light emitting diode (LED) putting the electrical power supply 62 in electrical communication with the visually perceptible element 42 or light emitting diode (LED). As both the eye target apparatus 22 and the alternative embodiment of the eye target apparatus 23 are preferably of a disposable one use type nature, the electrical switch 60 can be as simple as an electrically insulating strip placed between either the positive (+) or negative (−) battery 62 terminal and the circuitry, wherein the insulating strip is removed to activate the visually perceptible element 42 or light emitting diode (LED), which will stay activated through the time period of the medical procedure, with either the eye target apparatus 22 and the alternative embodiment of the eye target apparatus 23 being disposed in the trash at the end of the time period for the medical procedure. However, the electrical switch 60 could be a conventional slide or push button type switch or an equivalent switch would be acceptable also, in any case the electrical switch is operative to function as a control to activate the visually perceptible element 42 or light emitting diode (LED). However, the electrical switch 60 could be optional or not included as the electrical power supply 62 could simply be left uninstalled out of either the eye target apparatus 22 and the alternative embodiment of the eye target apparatus 23 prior to use and the electrical power supply 62 installed at the time of use of either the eye target apparatus 22 and the alternative embodiment of the eye target apparatus 23. The circuitry 59 also includes the resistor 61 that can either be fixed in resistance or variable in resistance, with resistance typically measured in Ohms, operationally the resister 61 can be used to limit the electrical power available to the visually perceptible element 42 or light emitting diode (LED) for controlling brightness of the visually perceptible element 42 or light emitting diode (LED), however, depending upon the electrical power available from the electrical power supply 62 and the electrical power requirements of the visually perceptible element 42 or light emitting diode (LED), the resistor 61 may or may not be required in the circuitry 59 as is well known in the electrical arts. The visually perceptible element 42 or light emitting diode (LED) is of a type that can utilize the aforementioned electrical power supply 62 and optional resistor 61 that is readily available commercially. In addition, the preferred color of the visually perceptible element 42 or light emitting diode (LED) is red for the desired visual differentiation against a bright white light 77 of the operating light, medical equipment, or device 76, that the operative eye 72 would experience from the eye surgeon's light for the medical procedure. Wherein, the patient 78 would experience seeing both the white background light 77 of the operating light, medical equipment, or device 76 and the visually perceptible element 42 or light emitting diode (LED), from the patient's 78 non operative eye 24 being in visual communication with the visually perceptible element 42 or light emitting diode (LED) and the patient's 78 operative eye 72 being in visual communication with the bright white light 77 of the operating light, medical equipment, or device 76. However, other colors different than red for the visually perceptible element 42 or light emitting diode (LED) would be acceptable as long as the preferred desired visual differentiation were achieved with the bright white light 77 of the operating light, medical equipment, or device 76. However, the visually perceptible element 42 can also function by being white in color by not having any differentiation from the operating light, medical equipment, or device 76. As a white visually perceptible element 42 can still act as a reference point for the patient's 78 non operative eye 24 thus still establishing the selected non operative eye 24 line of sight focus axis 26 position generally resulting in a like operative eye 72 (as shown in FIG. 11) line of sight focus axis 74 (as shown in FIG. 11) position, as the patient's 78 eyes normally act in coordination for movement and stability in remaining in the selected line of sight focus axis position(s) or further selected line of sight focus axis position(s) and with both the non operative eye 24 and the operative eye 72 remaining more stable at the selected line of sight focus axis position(s). Note that the electrical communication 63 between the circuitry 59 and the visually perceptible element 42 or light emitting diode (LED) as shown in FIG. 8 is not shown in FIGS. 1 through 7, however, the electrical communication 63 could be internal, within, or external to the housing 28 as long as the electrical communication is maintained between the circuitry 59 and the visually perceptible element 42 or light emitting diode (LED), as the visually perceptible element 42 or light emitting diode (LED) is moved within the plane 32 to any selected position. The electrical communication 63 may be flexible wiring, or may be a series of sliding electrical conducting strips, or may be fixed as in the case of the circuitry 59 within the housing 65 moving in conjunction with the visually perceptible element 42 or light emitting diode (LED), when the circuitry 59 within the housing 65 is mounted to or is adjacent to the visually perceptible element 42 or light emitting diode (LED).

As previously mentioned, as both the eye target apparatus 22 and the alternative embodiment of the eye target apparatus 23 are preferably of a disposable one use type nature for medical procedures, thus the construction of the eye target apparatus 22 and the alternative embodiment of the eye target apparatus 23 would be such that it is assembled, sterilized, and packaged in a sterile package 68, as shown in FIG. 2, as is known in the medical arts. Thus, in use the eye target apparatus 22 and the alternative embodiment of the eye target apparatus 23 would be removed from the sterile package 68 just prior to the medical procedure, then used for the medical procedure, and disposed of in the trash. Alternatively, it would be acceptable to reuse both the eye target apparatus 22 and the alternative embodiment of the eye target apparatus 23 by resterilizing and then resterile packaging after each use if resterilizing and resterile packaging proved economically desirable.

Moving in detail to the means 44 for moving the visually perceptible element 42 within the plane 32, which would apply to both the eye target apparatus 22 and the alternative embodiment of the eye target apparatus 23, preferably the housing 28 for occluding substantially all visual perception from the exterior environment 39 for the non operative eye 24. The means 44 housing would include a cover 40 with an aperture 41, with the cover 40 also including an internal surface 30 that forms a plane 32 positioned approximately perpendicular to the non operative eye 24 focus line of sight axis 26 as the non operative eye 24 focus line of sight axis 26 is positioned approximately in a normal looking straight ahead position from the patient's 78 facial contour 27 as shown in FIGS. 5 and 7. Also included in the means 44 for moving the visually perceptible element 42 within the plane 32 is a cap 50 having a slidable engagement 47 with the cover 40, with the cap 50 being sized and configured in conjunction with the slidable engagement 47 to substantially occlude the aperture 41 from allowing substantially all visual perception from the exterior environment 39 to the non operative eye 24 through a selected range of the slidable engagement 47 between the cap 50 and cover 40. Further in the means 44 the visually perceptible element 42 is disposed upon the cap 50 being in visual communication with the non operative eye 24 through a selected range of the slidable engagement 47 between the cap 50 and cover 40 through the focus line of sight axis 26 being aligned with an eye lens 25 of the non operative eye 24. The materials of construction for the cap 50 are similar to those of the aforementioned housing 28. The visually perceptible element 42 is positioned to be adjacent to the cover 40 internal surface 30. The disposition of the visually perceptible element 42 upon the cap 50 is preferably accomplished by shrink or close clearance fit, adhesive, snap fit, a retainer element, or the like, with the materials of construction for the visually perceptible element 42 adhesive being like the materials of construction for the aforementioned adhesive 49. Wherein the eye target apparatus 22 and the alternative embodiment of the eye target apparatus 23 are operational to help the non operative eye 24 focus on a selected line of sight focus axis 26 position upon the visually perceptible element 42 with the result in assisting in the operative eye 72 to achieve a stable selected line of sight focus axis 74 position with minimal operative eye 72 movement from the selected line of sight focus axis 74 position. Further, the non operative eye 24 focusing on subsequent selected line of sight focus axis 26 position(s) upon the visually perceptible element 42 are possible as required for the medical procedures. Wherein the selected focus line of sight axis 74 (as shown in FIG. 11) position and line of sight position stability of the operative eye 72 (as shown in FIG. 11) acts in conjunction with the occluded or non operative eye 24 selected line of sight focus axis 26 position by both of the patient's 78 eyes generally acting in coordination. Further included the means 44 for moving the visually perceptible element 42 within the plane 32 is an optional lockable element 43 that is adjacent to the cover 40 and the cap 50. The lockable element 43 is further accessible from the exterior environment 39, with the lockable element 43 being operational to help prevent relative movement between the cap 50 and the cover 40 at the slidable engagement 47, when the lockable element 43 is in a locked state after the cap 50 is moved to a selected position and the lockable element 43 allowing free relative movement between the cap 50 and the cover 40 when the lockable element 43 is in an unlocked state. The construction of the lockable element 43 can be varied as long as the aforementioned function is maintained, in one embodiment as is shown in FIGS. 5 and 7 the lockable element 43 is simply a thumb screw that clamps at the slidable engagement 47 to help prevent relative movement between the cap 50 and the cover 40. The materials of construction of the lockable element 43 are similar to those of the aforementioned housing 28. A further optional refinement included in the means 44 for moving the visually perceptible element 42 within the plane 32 is an indicia 70 relative to the eye target apparatus 22 as shown in FIGS. 1, 2, 3, 4, and 5, wherein the indicia 70 is disposed upon the cover 40 and cap 50 to be visible from the exterior environment 39. The indicia 70 relative to the alternative embodiment of the eye target apparatus 23 as shown in FIGS. 6 and 7 is disposed upon the cap 50 and a cover retainer element 64. The indicia 70 for both the eye target apparatus 22 and the alternative embodiment of the eye target apparatus 23 is operational to indicate the relative selected position between the cap 50 and the cover 40 through the range of the slidable engagement 47 for the eye target apparatus 22 and the relative selected position between the cap 50 and the cover retainer element 64 through the range of the slidable engagement 47 for the alternative embodiment of the eye target apparatus 23. The indicia 70 can be integrally molded to the cap 50, and/or cover 40, and/or the cover retainer element 64, or can be painted, or a sticker(s) can be affixed to the aforementioned elements with the requirement of the paint and/or sticker(s) being suitable for medical use and sterilizable. A yet further optional refinement included the means 44 for moving the visually perceptible element 42 within the plane 32 is a finger grip or protrusion 52 disposed upon the cap 50 applying to both the eye target apparatus 22 and the alternative embodiment of the eye target apparatus 23 with the finger grip 52 being positioned to be accessible from the external environment 39, wherein the finger grip 52 is operational to assist in manually moving the cap 50 relative to the cover 40. The materials of construction for the finger grip 52 would be similar to the aforementioned housing 28.

In addition, for the means 44 for moving the visually perceptible element 42 within the plane 32, relative to the eye target apparatus 22 as shown in FIGS. 1, 2, 3, 4, and 5, further included is a slidable cap retainer element 54 that is adjacent to the cap 50, as best shown in FIG. 5. The attachment of the slidable cap retainer element 54 to the cap 50 is preferably accomplished at the slidable cap retainer element extension 58 by shrink or close clearance fit, adhesive, snap fit, a retainer element or the like, with the materials of construction for the slidable cap retainer element extension 58 adhesive being like the materials of construction for the aforementioned adhesive 49. The slidable cap retainer element 54 also includes an aperture 56 within the slidable cap retainer element extension 58 and within the slidable cap retainer element 54, with the aperture 56 providing for visual communication between the visually perceptible element 42 and the non operative eye 24. As the slidable cap retainer element 54 moves in conjunction with the cap 50 as indicated by arrows 46 and arrows 48 there is formed a slidable engagement 47 between the cover 40 and the cap 50 and another slidable engagement 51 between the slidable cap retainer element 54 and the cover 40, again as best shown in FIG. 5. The movement of the cap 50 and the slidable cap retainer element 54 is relative to the cover 40 wherein the direction of movement is not limited by what arrows 46 and 48 indicate, as the allowable movement is anywhere or omnidirectional within the housing plane 32 with the arrows 46 and 48 only indicating the outer range of movement as best shown in FIGS. 1, 3, and 4. Also, both of the slidable engagements 47 and 51 act to occlude substantially all visual perception to the non operative eye 24 from the exterior environment 39 over the range of omnidirectional movement of the cap 50 and slidable cap retainer element 54 relative to the cover 40. The slidable cap retainer element 54 is positioned to slidably engage 51 the cover 40 on a side opposite of the cap 50 and cover 40 slidable engagement 47. The cap retainer element 54 is operational to help further retain the cap 50 to the cover 40 during relative movement between the cap 50 and the cover 40. The materials of construction of the slidable cap retainer element 54 including the slidable cap retainer element extension 58 would be similar to the aforementioned housing 28.

Further, in addition, for the means 44 for moving the visually perceptible element 42 within the plane 32, relative to the alternative embodiment of the eye target apparatus 23 as shown in FIGS. 6 and 7, further included is a cover retainer element 64 that is adjacent to the cover 40, as best shown in FIG. 7. Attachment of the cover retainer element 64 to the cover 40 is preferably at an outer peripheral cover retainer element extension 57 as best shown in FIG. 7, the attachment is also preferably by shrink or close clearance fit, adhesive, snap fit, a retainer element or the like, with the materials of construction for the outer peripheral cover retainer element extension 57 adhesive being like the materials of construction for the aforementioned adhesive 49. The cover retainer element 64 also includes an aperture 66 that provides clearance for the omnidirectional movement of the cap 50 relative to the cover 40. As the cover retainer element 64 is adjacent to the cover 40, the cover retainer element 64 and the cover 40 "sandwich" the cap 50 in a slidable engagement 53 that is between the cover retainer element 64 and the cap 50 and a slidable engagement 47 between the cap 50 and the cover 40 as best shown in FIG. 7, with the limits on range of the slidable engagement movements 47 and 53 indicated by arrows 46 and arrows 48 as best shown in FIG. 6. The movement of the cap 50 relative to both the cover 40 and the cover retainer element 64 is such that the range of movement is not limited by what arrows 46 and 48 indicate, as the allowable movement is anywhere or omnidirectional within the housing plane 32 with the arrows 46 and 48 only indicating the outer range of movement as best shown in FIG. 6. Also, both of the slidable engagements 47 and 53 act to occlude substantially all visual perception to the non operative eye 24 from the exterior environment 39 over the range of omnidirectional movement of the cap 50 relative to both the cover 40 and the cover retainer element 64. The cover retainer element 64 is positioned to slidably engage 53 the cap 50 on a side opposite of the cap 50 and cover 40 slidable engagement 47. The cover retainer element 64 is operational to help further retain the cap 50 to the cover 40 during relative movement between the cap 50 and the cover 40. The materials of construction for the cover retainer element 64 including the cover retainer element extension 57 are similar to the aforementioned housing 28.

Method of Use

With specific reference to FIGS. 9, 10, and 11 a method of using both the eye target apparatus 22 as structurally shown in FIGS. 1, 2, 3, 4, and 5, and the alternative embodiment of the eye target apparatus 23 as structurally shown in FIGS. 6 and 7, for use in helping to control an operative eye 72 focus line of sight axis 74 position during medical procedures on the operative eye 72. With FIG. 9 being a flow chart illustrating diagrammatically the broad concepts according to the methodology of using both the eye target apparatus 22 and the alternative embodiment of the eye target apparatus 23 and FIG. 10 being a continuation of FIG. 9 showing the flow chart illustrating diagrammatically the broad concepts according to the methodology of using both the eye target apparatus 22 and the alternative embodiment of the eye target apparatus 23 comprising the following steps. Further, FIG. 11 shows a use view showing either the eye target apparatus 22 or the alternative embodiment of the eye target apparatus 23 positioned on the patient's 78 facial contour 27 over the non operative eye 24 (hidden in FIG. 11 by the eye target apparatus 22 or 23) with the patient's 78 operative eye 72 exposed to the bright white light 77 of the operating light, medical equipment, or device, sometimes termed microscope 76 with the patient 78 in a supine position on the operating table 80 with a sterile drape 82 placed over the patient 78 with only the patient's 78 operative eye 72 and non operative eye 24 exposed.

The first use step 100 is to position the patient 78 who is in need of a medical procedure on their operative eye 72, as an example such as cataract removal, lens implants, vision corrective surgery, injury repair, and the like by placing the patient 78 in the supine position to be proximate to the required operating light, medical equipment, or device 76, as an example a microscope to aid in performing eye surgery as best shown in FIG. 11 with the operating light, medical equipment, or device 76 able to be positioned over the operative eye 72. The next use step 102 is to locate the operating light, medical equipment, or device 76 including an activated bright light source 77 over the operative eye 72 of the patient 78 as best shown in FIG. 11. A further use step 104 is to provide the eye target apparatus, being either the eye target apparatus 22 as shown in FIGS. 1-5 or the alternative embodiment of the eye target apparatus 23 as shown in FIGS. 6 and 7 that each includes a housing 28 for occluding substantially all visual perception from an exterior environment 39 for the non operative eye 24. The housing 28 includes a cover 40, the cover 40 also includes an internal surface 30 that forms a plane 32 positioned approximately perpendicular to the non operative eye 24 line of sight axis 26. Also, included is a visually perceptible element 42 that is adjacent to the cover 40 internal surface 30, the visually perceptible element 42 being in visual communication with the non operative eye 24, with the visually perceptible element 42 being normally unactivated or not being visually perceptible. Also included is a means 44 for moving the visually perceptible element 42 within the plane 32 to any selected position or omnidirectionally within the outer limits of movement depicted by arrows 46 and 48 as best shown in FIGS. 1, 3, 4, and 6. Also within use step 104 is a step of placing the eye target apparatus being either the eye target apparatus 22 as shown in FIGS. 1-5 or the alternative embodiment of the eye target apparatus 23 as shown in FIGS. 6 and 7 over the non operative eye 24 of the patient 78 to occlude substantially all visual perception from the exterior environment 39 for the non operative eye 24 as best shown in FIG. 11. Preferably, either the target apparatus 22 or the alternative embodiment of the eye target apparatus 23 are affixed to the patient's 78 facial contour 27 by the adhesive 49 on the housing mounting pad 36 to help secure the target apparatus 22 or the alternative embodiment of the eye target apparatus 23 over the patient's 78 non operative eye 24 thereby occluding substantially all visual perception from the external environment 39 to the non operative eye 24.

A next further use step 106 is instructing the patient 78 to open their operative eye 72 and non operative 24 eyes for a selected time period that is of such duration to allow the patient 78 to adjust visually to the bright white light 77 of the operating light, medical equipment, or device 76 that has been placed or positioned over the patient's 78 operative eye 72 as best shown in FIG. 11. Subsequently, the following use step 108 is in activating the visually perceptible element 42 to be in visual communication with the non operative eye 24 at the conclusion of the selected time period, wherein activating the visually perceptible element 42 preferably includes lighting the visually perceptible element 42 (LED) in the circuitry 59 by initiating electrical communication between the electrical power supply 62 and the visually perceptible element 42 (LED), which is preferably done by utilizing the electrical switch 60 to activate the circuitry 59. Thus, at this point the patient 78 has their operative eye 72 visually exposed to the bright white light 77 of the operating light, medical equipment, or device 76 and their non operative eye 24 visually exposed to the activated visually perceptible element 42 (LED), wherein the patient's 78 mental visual image combines the bright white light 77 of the operating light, medical equipment, or device 76 and the visually perceptible element 42 (LED) into a singular image. Further, a use step 110 is to confirm that the patient 78 sees a mental image the visually perceptible element 42 (LED) substantially centered in the light source 77 of the operating light, medical equipment, or device 76 to establish proper patient 78 operative eye 72 focus line of sight axis 74 and non operative eye 24 focus line of sight axis 26. The purpose of step 110 is to prevent the patient 78 from converging their gaze on the visually perceptible element 42 causing the operative eye 72 to move out of position to have a correct initial starting position for both the operative eye 72 focus line of sight axis 74 and the non operative eye 24 focus line of sight axis 26. Next, a use step 112 of manually moving, by typically the eye surgeon or another the visually perceptible element 42 to a selected position to further establish a desired patient 78 operative eye 72 focus line of sight axis 74 position, manually moving the visually perceptible element 42 is accomplished through the means 44 for moving the visually perceptible element 42 within the plane 32 as previously described by preferably grasping the slidable cap 50 finger grip 52 and manually moving the cap 50 to a selected position omnidirectionally within the outer range of movement depicted by arrows 46 and 48 as best shown in FIGS. 1, 3, 4, and 6. The aforementioned movement of the cap 50 actually is allowing the non operative eye 24 to focus in conjunction with the non operative eye 24 focus line of sight axis 26 upon the visually perceptible element 42 within the plane 32 and by moving the cap 50 and thus the visually perceptible element 42 within the plane 32 to a selected position, the non operative eye 24 focus line of sight axis 26 is in a selected position also. What the patient 78 actually sees is the visually perceptible element 42 substantially in the central portion of the bright white light 77 of the operating light, medical equipment, or device 76.

A further subsequent use step 113 is in performing the required medical procedure on the operative eye 72 by the eye surgeon and/or other medical personnel for the patient 78. These medical procedures can include medical procedures such as cataract removal, lens implants, vision corrective surgery, injury repair, and the like, which are typically done under local anesthesia. Thus, with local anesthesia the patient 78 takes an active part in assisting and cooperating with the eye surgeon and/or other medical personal during the course of the medical procedure. The patient 78 is then instructed that during the medical procedure that the bright white light 77 of the operating light, medical equipment, or device 76 may appear to be moving but to continue focusing upon the visually perceptible element 42, thus enabling the non operative eye 24 to remain in a more stable focus line of sight axis 26 position while the eye surgeon or another adjusts the bright white light 77 of the operating light, medical equipment, or device 76 during the course of the medical procedure. In other words, the visually perceptible element 42 acts as a visual reference point for the non operative eye 24 of the patient 78 during the course of the medical procedure. As the patient's 78 eyes being the non operative eye 24 and operative eye 72 generally act in coordination or are contralateral to one another, the operative eye 72 focus line of sight axis 74 will generally follow the non operative eye 24 focus line of sight axis 26 and will also tend to have the same stability at helping to hold both the non operative eye 24 focus line of sight axis 26 and the operative eye 72 focus line of sight axis 74, which is of interest to the eye surgeon and others during the medical procedure.

It is import that the patient 78 have a visual reference point with focusing upon the visually perceptible element 42 for the non operative eye 24, as typically during the course of the medical procedure on the operative eye 72, the patient 78 can have diminished visual capability in the operative eye 72 (as compared to the non operative eye 24) and can become visually disoriented, especially if the bright white light 77 of the operating light, medical equipment, or device 76 is moved during the medical procedure. This can result in the operative eye 72 changing its focus line of sight position axis 74 arbitrarily during the medical procedure, resulting in making the eye surgery more difficult and lengthy potentially causing additional medical complications. Thus, in an optional use step 116 via 152 from step 113, the patient 78 is instructed to focus both their non operative eye 24 and operative eye 72 steady upon the visually perceptible element 42 to achieve increased steadiness of the patient's 78 non operative eye 24 focus line of sight axis 26 position and operative eye 72 line of sight axis 74 position while the patient 78 perceives movement or position change of the bright white light 77 of the operating light, medical equipment, or device 76 with the typically diminished visual capacity of the patient's operative eye 72 in an effort to minimize additional medical complications during the course of the medical procedure. Further, in optional use step 114 via 150 from step 113 of instructing the patient 78 to move their operative eye 72 line of sight axis 74 position and non operative eye 24 focus line of sight axis 26 position relative to the visually perceptible element 42 for a selected period using the visually perceptible element 42 as a visual reference focus line of sight point for both the operative eye 72 and the non operative eye 24. Thus, step 114 allows the eye surgeon or another to make timely relative operative eye 72 movement of the focus line of sight axis 74 during the medical procedure with the patient 78 able to use the visually perceptible element 42 as a static visual reference focus line of sight point and have the patient 78 respond to instructions such as; look above, look below, look to the right, and/or look to the left of the visually perceptible element 42, giving the eye surgeon or another some measure of control over controlling the patient's 78 operative eye 72 relative movement of the focus line of sight axis 74 during the medical procedure. Also, the eye surgeon or another can reestablish the original operative eye 72 focus line of sight axis 74 position by instructing the patient 78 to refocus both their operative eye 72 focus line of sight axis 74 position and non operative eye 24 focus line of sight axis position 26 back upon the visually perceptible element 42.

Note that during the medical procedure step 113 wherein the medical procedure is performed upon the operative eye 72, optional repetition of the aforementioned step 112 via 154 from either aforementioned step 114 or aforementioned step 116 can be repeated as many times as needed to complete the medical procedure step 113 and in addition aforementioned steps 114 and/or 116 can be repeated also as many times as needed to complete the medical procedure step 113. Also, the sequence of the aforementioned steps 112, 114, and 116 can be in any order as may be deemed necessary by the eye surgeon or another during performance of the medical procedure step 113. Either the eye target apparatus 22 or the alternative embodiment of the eye target apparatus 23 are removed from the patient's 78 facial contour 27 at the final completion of the medical procedure step 113.

CONCLUSION

Accordingly, the present invention of an Eye Target Apparatus has been described with some degree of particularity directed to the embodiment(s) of the present invention. It should be appreciated, though, that the present invention is defined by the following claims construed in light of the prior art so modifications or changes may be made to the exemplary embodiment(s) of the present invention without departing from the inventive concepts contained therein.

The invention claimed is:

1. An eye target apparatus for use in helping to control an operative eye focus line of sight axis position during medical procedures on the operative eye, comprising:
   (a) a housing for occluding substantially all visual perception from an exterior environment for a non operative eye, said housing including a cover, said cover also including an internal surface that forms a plane positioned approximately perpendicular to the non operative eye line of sight axis;
   (b) a visually perceptible element adjacent to said cover internal surface being in visual communication with the non operative eye; and
   (c) means for moving said visually perceptible element within the plane to any selected position, wherein said eye target apparatus is operational to help the non operative eye focus on a selected line of sight focus axis position upon said visually perceptible element with the result in assisting in the operative eye achieving a stable selected line of sight focus axis position with minimal operative eye movement from the selected line of sight focus axis position.

2. An eye target apparatus according to claim 1 wherein said visually perceptible element is a color that is visually perceptible against a white background.

3. An eye target apparatus according to claim 1 wherein said visually perceptible element is a light emitting diode (LED) including circuitry in electrical communication to said light emitting diode (LED), said circuitry being disposed on an exterior of said housing.

4. An eye target apparatus according to claim 3 wherein said light emitting diode (LED) is red in color.

5. An eye target apparatus according to claim 3 wherein said circuitry includes a control operative to activate said light emitting diode (LED).

6. An eye target apparatus according to claim 1 wherein said housing is constructed of a surrounding sidewall extending from said cover to define a housing interior separated from the exterior environment, said surrounding sidewall including an end portion opposite of said cover that creates an opening communicating between the housing interior and the exterior environment.

7. An eye target apparatus according to claim 6 further comprising a flange portion adjacent to said surrounding sidewall end portion, wherein said flange portion is operational to rest against a patient's facial contour adjacent to the non operative eye.

8. An eye target apparatus according to claim 7 further comprising a resilient housing mounting pad adjacent to said flange portion, wherein said mounting pad is operational to conform to a patient's facial contour adjacent to the non operative eye.

9. An eye target apparatus according to claim 8 wherein said resilient housing mounting pad includes an adhesive, wherein said adhesive is operational to removably attach said resilient housing mounting pad to the patient's facial contour adjacent to the non operative eye.

10. An eye target apparatus according to claim 1 further comprising a sterile package that contains said eye target apparatus.

11. An eye target apparatus for use in helping to control an operative eye focus line of sight axis position during medical procedures on the operative eye, comprising:
    (a) a housing for occluding substantially all visual perception from an exterior environment for a non operative eye, said housing including a cover with an aperture, said cover also including an internal surface that forms a plane positioned approximately perpendicular to the non operative eye line of sight axis;
    (b) a cap having a slidable engagement with said cover, said cap being sized and configured to substantially occlude said aperture through a selected range of said slidable engagement; and
    (c) a visually perceptible element disposed upon said cap being in visual communication with the non operative eye, said visually perceptible element being positioned to be adjacent to said cover internal surface, wherein said eye target apparatus is operational to help the non operative eye focus on a selected line of sight focus axis position upon said visually perceptible element with the result in assisting in the operative eye achieving a stable selected line of sight focus axis position with minimal operative eye movement from the selected line of sight focus axis position.

12. An eye target apparatus according to claim 11 further comprising a lockable element adjacent to said cover and said cap, said lockable element being further accessible from the exterior environment, wherein said lockable element is operational to help prevent relative movement between said cap and said cover, when said lockable element is in a locked state after said cap is moved to a selected position and said lockable element allowing free relative movement between said cap and said cover when said lockable element is in an unlocked state.

13. An eye target apparatus according to claim 11 further comprising indicia disposed upon said cover and said cap to be visible from the exterior environment, said indicia being operational to indicate the relative selected position between said cap and said cover.

14. An eye target apparatus according to claim 11 wherein said cap has a finger grip disposed upon said cap being positioned to be accessible from the external environment, wherein said finger grip is operational to assist in moving said cap relative to said cover.

15. An eye target apparatus according to claim 11 further comprising a cap retainer element that is adjacent to said cap, said cap retainer element is positioned to slidably engage said cover on a side opposite of said cap slidable engagement, wherein said cap retainer element is operational to help further retain said cap to said cover during relative movement between said cap and said cover.

16. An eye target apparatus according to claim 11 further comprising a cover retainer element that is adjacent to said cover, said cover retainer element being positioned to slidably engage said cap on a side opposite of said cap slidable engagement, wherein said cover retainer element is operational to help further retain said cap to said cover during relative movement between said cap and said cover.

17. An eye target apparatus according to claim 11 wherein said visually perceptible element is a color that is visually perceptible against a white background.

18. An eye target apparatus according to claim 11 wherein said visually perceptible element is a light emitting diode (LED) including circuitry in electrical communication to said light emitting diode (LED), said circuitry being disposed on an exterior of said housing.

19. An eye target apparatus according to claim 18 wherein said light emitting diode (LED) is red in color.

20. An eye target apparatus according to claim 18 wherein said circuitry includes a control operative to activate said light emitting diode (LED).

21. An eye target apparatus according to claim 11 wherein said housing is constructed of a surrounding sidewall extending from said cover to define a housing interior separated from the exterior environment, said surrounding sidewall including an end portion opposite of said cover that creates an opening communicating between the housing interior and the exterior environment.

22. An eye target apparatus according to claim 21 further comprising a flange portion adjacent to said surrounding sidewall end portion, wherein said flange portion is operational to rest against a patient's facial contour adjacent to the non operative eye.

23. An eye target apparatus according to claim 22 further comprising a resilient housing mounting pad adjacent to said flange portion, wherein said mounting pad is operational to conform to a patient's facial contour adjacent to the non operative eye.

24. An eye target apparatus according to claim 23 wherein said resilient housing mounting pad includes an adhesive, wherein said adhesive is operational to removably attach said resilient housing mounting pad to the patient's facial contour adjacent to the non operative eye.

25. An eye target apparatus according to claim 11 further comprising a sterile package that contains said eye target apparatus.

26. A method of using an eye target apparatus for use in helping to control an operative eye focus line of sight axis position during medical procedures on the operative eye, comprising the steps of:
    (a) positioning a patient;
    (b) locating a medical device including a light source over the operative eye of the patient;
    (c) providing an eye target apparatus that includes a housing for occluding substantially all visual perception from an exterior environment for a non operative eye, said housing including a cover, said cover also including an internal surface that forms a plane positioned approximately perpendicular to the non operative eye focus line of sight axis, a visually perceptible element adjacent to said cover internal surface being in visual communication with the non operative eye, said visually perceptible element being normally unactivated, and a means for moving said visually perceptible element within the plane to any selected position;
    (d) placing said eye target apparatus over the non operative eye of the patient to occlude substantially all visual perception from the exterior environment for the non operative eye;
    (e) instructing the patient to open their operative and non operative eyes for a selected period;
    (f) activating said visually perceptible element at the conclusion of said selected period;
    (g) confirming that the patient sees said visually perceptible element substantially centered in said light source to establish proper patient operative eye and non operative eye focus line of sight axes;

(h) moving said visually perceptible element to a selected position to further establish a desired patient operative eye focus line of sight axis position; and (i) performing required medical procedure on the operative eye.

27. A method of using an eye target apparatus according to claim 26 further comprising a subsequent step of instructing the patient to keep their operative eye and non operative eye focus line of sight axis positions steady upon said visually perceptible element when said light source changes position.

28. A method of using an eye target apparatus according to claim 26 further comprising a subsequent step of instructing the patient to move their operative eye and non operative eye focus line of sight axis positions relative to said visually perceptible element for a selected period using said visually perceptible element as a reference focus line of sight point for both the operative eye and the non operative eye.

* * * * *